United States Patent [19]

Wulf

[11] Patent Number: 5,385,560
[45] Date of Patent: Jan. 31, 1995

[54] REDUCER FOR CANNULAE
[75] Inventor: Thomas Wulf, Hamburg, Germany
[73] Assignee: Ethicon Endo-Surgery, Cincinnati, Ohio
[21] Appl. No.: 128,620
[22] Filed: Sep. 28, 1993
[30] Foreign Application Priority Data Oct. 13, 1992 [DE] Germany .................... 4234452

[51] Int. Cl.6 .................. A61M 5/00; A61M 25/00; A61M 5/178
[52] U.S. Cl. .................. 604/264; 604/256; 604/167
[58] Field of Search .............. 128/912; 604/49, 51, 604/93, 158, 164, 256, 264

[56] References Cited

U.S. PATENT DOCUMENTS

| | | | |
|---|---|---|---|
| 4,112,932 | 9/1978 | Chiulli | 604/264 |
| 4,715,360 | 12/1987 | Akui et al. | 128/4 |
| 4,723,550 | 2/1988 | Bales et al. | 604/256 |
| 4,944,732 | 7/1990 | Russo | 604/256 |
| 4,972,827 | 11/1990 | Kishi et al. | 128/3 |
| 5,104,383 | 4/1992 | Shichman | 604/49 |
| 5,209,736 | 5/1993 | Stephens et al. | 604/158 |
| 5,269,772 | 12/1993 | Wilk | 604/264 |

FOREIGN PATENT DOCUMENTS 1863280 9/1962 Germany .

Primary Examiner—C. Fred Rosenbaum
Assistant Examiner—Frank Wilkens, III
Attorney, Agent, or Firm—Paul A. Coletti

[57] ABSTRACT

A reducer for trocar cannulae includes a covering cap which can be secured on the handle of a cannula and which has a socket engaging with a distal end to the handle provided for the shaft of operating instruments. The proximal end face of the socket is sealed off via a wall provided with at least two openings. Seals for shafts of operating instruments of smaller diameter are allocated to the openings.

9 Claims, 1 Drawing Sheet

REDUCER FOR CANNULAE

PRIORITY APPLICATION

This application is based on DE 4234452.2 filed Oct. 13, 1992.

FIELD OF THE INVENTION

The invention relates to a reducer for cannulae (trocar sleeves) used in endoscopic surgery.

BACKGROUND OF THE INVENTION

In endoscopic operation techniques, surgical instruments and observation equipment are introduced into the inside of the body through cannulae. A cannula is inserted through the tissue layers, for example the abdominal wall, with the help of a trocar, which is later removed. In its distal zone, a cannula consists of a tube to whose proximal end a top piece or handle is attached, which top piece is located outside the body. In the case of operations, in the abdominal area in particular, it is necessary to introduce a gas, for example carbon dioxide, under pressure into the inside of the body. This insufflation causes the abdominal wall to become better detached from the internal organs and the organs are thereby easier to access for the operation. To this end, the opening at the distal end face of the top piece is provided with a seal in order that the gas does not escape from the inside of the body via this opening.

Also located in the top piece there may be a closure device which seals off the opening if no operation instrument is inserted. Finally, the top piece can be provided with a connection for the supply of the compressed insufflation gas.

The trocar causes a puncture wound which is much smaller than the incisions which are customary in open surgery. Even the use of cannulae with a larger diameter requires a very small incision. Such larger cannulae are necessary if certain instruments, such as ligating clip appliers, are also to be used in endoscopic operations.

As the seal in the handle of the cannula must lie against the shaft of the operation instrument, it is provided with a relatively larger opening, so that an operation instrument with a relatively smaller diameter cannot thus be introduced into a large cannula in such a way that the seal is able to perform its function.

SUMMARY OF THE INVENTION

The object of the invention is to provide the possibility of opening a more flexible field of application to cannulae with a large diameters.

This object is achieved by a reducer for cannulae which includes a covering cap which can be secured on the top or handle piece of a larger cannula. The distal end of a socket engages at the seal of the cannula, so that the reducer is tightly connected to the top piece of the cannula. The proximal end face of the socket is sealed off via a wall provided with at least two openings. These openings form seals for shafts of smaller diameter operation instruments being allocated to the openings. The result is that, depending on the number of openings in the wall, several operating instruments of smaller diameters can be guided simultaneously through the large cannula. It is therefore not necessary to introduce a separate cannula through the body wall for each individual operating instrument, a factor of considerable advantage to the patient. With many operating procedure techniques, the fact that the instruments can be brought together to the operation area in a small space is also favorable.

The wall preferably consists of an elastic plastics material, the edges of the openings serving as sealing surfaces. As a result, the structure of the reducer according to the invention is particularly simple and inexpensive. The wall can be reinforced between the openings by a stabilization section, in order that the shape and the sealing behavior of neighboring openings are not unfavorably influenced by the insertion of an operating instrument into a given opening.

In a preferred version, a closure cap is allocated to at least one opening. If there are two openings in the reducer, one opening can be sealed off by the closure cap, so that in this case a large cannula provided with such a reducer can be used without problems for a single operating instrument within the reducer shaft. The closure cap can be, for example, a stopper whose diameter is matched to the opening, or can be designed as a sealing disk, which elastically abuts against the edge of the reducer opening and which can be flipped away upon the introduction of an operation instrument.

DESCRIPTION OF THE DRAWINGS

The invention is described more precisely below with reference to an embodiment. Shown is.

DETAILED DESCRIPTION OF THE INVENTION

Figure 1:
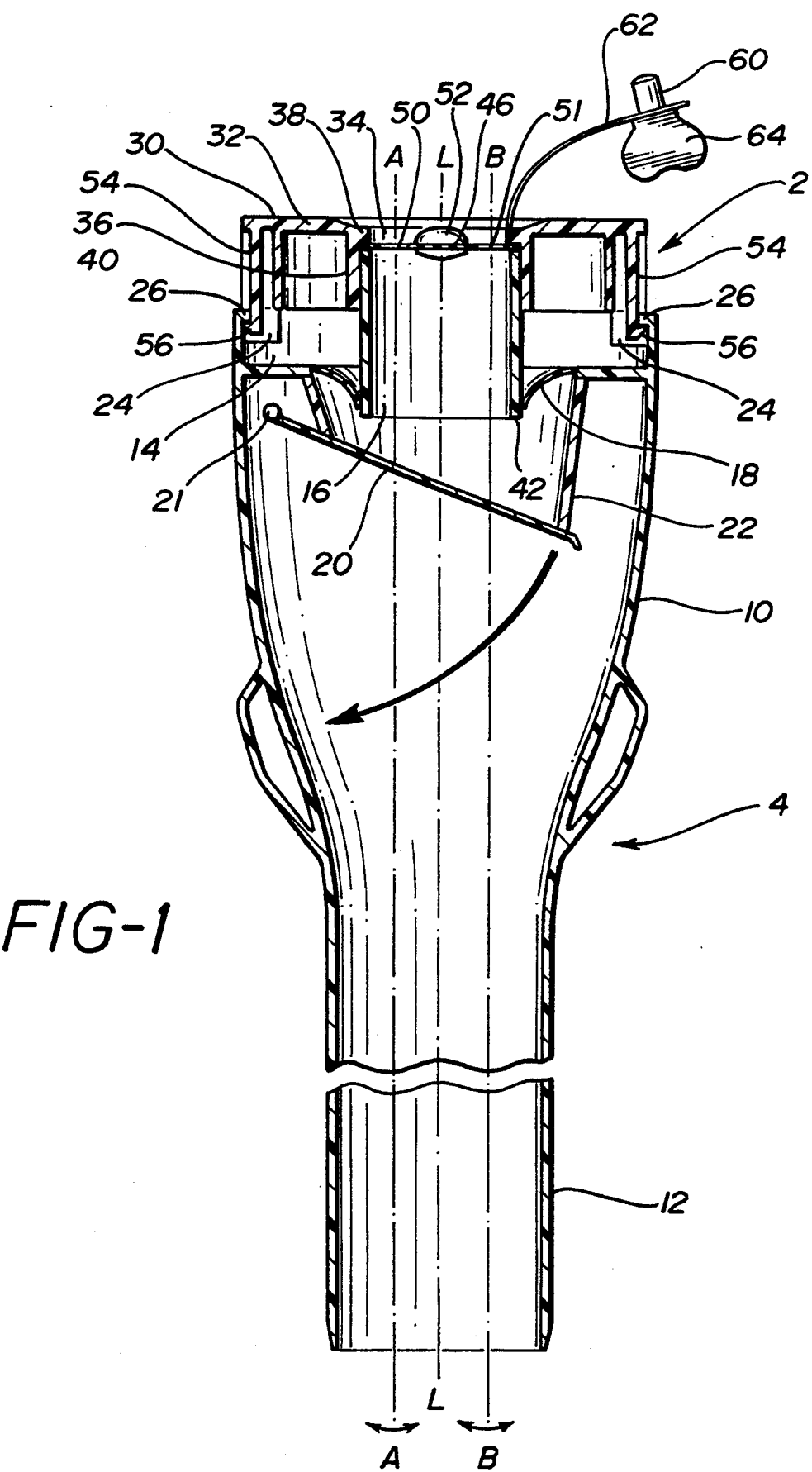
FIG. 1 is a longitudinal section of a reducer according to the invention, which is fitted onto a cannula, in the plane of the longitudinal axis L—L.

In the representation reproduced in FIG. 1, a reducer 2 according to the invention is fitted onto a cannula 4, the cannula 4 being a cannula with a larger diameter, for example with a diameter of the order of 30 mm–40 mm.

The cannula 4 comprises a top piece 10 to which an essentially cylindrical tube 12 is connected. The tube 12 penetrates the body wall with the help of an obturator, which is later removed, while the top piece or cannula handle is located outside the body during an operation. The top piece 10 has a proximal end wall 14 which is provided with a circular opening 16 lying symmetrically relative to the longitudinal axis L—L. Attached to the underside of the proximal end wall 14 is an annular seal 18 whose inner diameter is less than that of the opening 16. The seal 18 consists of an elastic plastics material, so that when an operating instrument is introduced through the opening 16 it lies against the seal 18 shaft. This prevents the compressed gas introduced into the body from escaping outwards through the gap between the shaft of the operating instrument and the edge of the opening 16. In relation to the internal diameter of the tube 12, the diameter of the opening 16 can also be larger than shown in FIG. 1 (cap to the interior of cylinder 12), better mobility for the operation instrument.

Arranged beneath opening 16 is a flap valve 20 which can be swivelled away downwards, i.e. in distal direction, about a swivel axis 21, as shown by the arrow. In the position shown in FIG. 1 the flap 20 elastically abuts against the distal end of a partition 22 which is shaped here essentially like the surface of a diagonally cut truncated cone. If no operating instrument is inserted, flap 20 is closed, as shown in FIG. 1, so that compressed gas cannot escape through the opening 16. Upon introduction of an operation instrument its distal end pushes the flap 20 downwards, and the flap then lies against the shaft of the instrument and no longer impedes its mobility. To improve the sealing effect, the flap 20 or the distal edge of the partition 22 can be provided with a sealing lining.

Provided at the proximal end wall 14 of the top piece 10 are recesses 24 which undercut projections 26. The projections 26 serve as counter-supports for stop hooks with which additional apparatus of a conventional cannula can be secured, for example a trocar obturator handle, with the help of which the puncture point can be produced for the insertion of the cannula.

The reducer 2 according to the invention includes a covering cap 30 whose cross-section is essentially matched to the cross-section of the top piece 10, and, unlike that of the tube 12, need not be circular. The covering cap 30 has a proximal end wall 32 with an opening 34. A tubular securing element 36, preferably concentric relative to the longitudinal axis L—L of the reducer 2 and the cannula 4, starts in distal direction from the proximal end wall 32. As its internal diameter is greater than the diameter of the opening 34, an annular projection 38 is formed at the proximal end wall 32.

A socket 40 (with preferably circular cross-section) is inserted into the tubular securing element 36. With its distal end 42, the socket 40 engages at the seal 18 of the top piece 10, so that, when the reducer 2 according to the invention is fitted onto the top piece 10 of the cannula 4, a gas-tight connection results. The socket 40 is in principal suitable for use with different types of cannula.

Clamped between the proximal edge of the socket 40 and the projection 38 is a wall 46 which contains at least two (preferably circular) openings. In the represented embodiment, two openings 50 and 51 are provided, through which operation instruments with a relatively smaller shaft diameter can be introduced through the socket 40 into the cannula 4 along the axis A—A or B—B. The wall 46 preferably consists of an elastic plastics material, for example silicone rubber, the edges of the openings 50, 51 serving as sealing surfaces which lie against the shaft of the operation instruments. If the elasticity of the plastics material is adequate, it is quite possible to use operating instruments with quite different shaft diameters and yet, nevertheless, achieve the desired sealing effect.

The wall 46 is preferably reinforced by a stabilization section 52 between the openings 50 and 51. The stabilization section 52 can consist of the same material as the wall 46 or of another, for example rigid, material. It can also be designed as a bar which is firmly connected at its two ends to the proximal end wall 32. The stabilization section 52 serves to minimize the influence of a particular operating instrument, which is introduced for example through the opening 50, on the size and shape of the adjacent opening 51 and on the elasticity and sealing behavior of the wall 46 in the area surrounding the opening 51. In this way, leaks are avoided, such as could otherwise occur upon movement of the operation instruments. On the other hand, the construction of the wall 46 from an elastic plastic material enables a large degree of mobility for the operating instruments, as indicated by the arrows at the distal end of the tube 12.

The proximal end face of the socket 40 is thus sealed off via the wall 46. This mode includes, on the one hand, the embodiment shown in FIG. 1 and, on the other hand, variants in which other gas-tight sections of the covering cap 30 lie between the proximal end of the socket 40 and the wall 46. Versions are also conceivable in which the sealing effect is achieved, not through the edges of the openings 50, 1 but via separate seals, for example O-rings.

To secure the reducer 2 according to the invention on the top piece 10 of cannula 4, stop hooks 54 are provided at the side wall of covering cap 30 in the embodiment. At their distal ends, the stop hooks 54 each have a projection 56 for engaging behind the projections 26 at the proximal end wall 14 of top piece 10. The distal zones of the stop hooks 54 can be pressed inwards in a radial direction against the elastic force of the stop hooks 54, in order to produce or break the stop connection. (As can be appreciated, other means of securing the reducer 2 on the top piece 10 can also be used instead of the stop hooks 54.)

A closure in the form of a stopper 60 is allocated to the opening 51, the diameter of the stopper 60 being matched to the diameter of the opening 51. The stopper 60 is connected to the covering cap 30 with the help of a flexible strip 62. In order to seal the opening 51, the stopper 60 can be inserted into the opening 51 with the help of the gripping part 64.

In an alternative version (not shown in FIG. 1), the closure consists of an elastic disk or flap which presses from below against the edge of the opening 50 or 51, a sealing effect being achieved upon selection of a suitable material for the disk or the wall 46. The disk is preferably hinged at one side so that, in a manner similar to the flap 20, it can be pressed away in distal direction upon introduction of an operation instrument. The disk can be made from the same plastics material as the wall 46. It can be made in one piece with the wall 46 or be connected to the wall 46 afterwards, for example via a securing point.

The reducer 2 according to the invention is applied by fitting it onto a cannula 4 previously introduced in conventional manner into the body tissue. The projections 56 of the stp hooks 54 engage at the projections 26 of the top piece 10 of the cannula 4, and ensure a secure mechanical connection. The socket 40 abuts against the seal 18 of the top piece 10 and ensures a gas-tight connection. During this process, the flap 20 is closed so that no gas can escape. In addition, should one of the openings 50 or 51 not be needed, it is closed with the associated stopper 60. An operation instrument of small shaft diameter can now be introduced through the other opening 50 or 51, thereby opening the flap 20. The sealing effect then results from the fact that the edge of the opening 50 or 51 lies against the shaft of the operation instrument. Several instruments can be used simultaneously where appropriate.

What is claimed is:

1. In combination:
   a cannula with open distal and proximal ends and a cylindrical opening extending through said ends, said cylindrical opening having a first diameter; and
   a reducer comprising:
   a covering cap secured to said cannula proximal end;
   a socket extending distally from said cap, said socket containing a distal end opening with a second diameter, said socket distal end opening extending into the opening in said cannula proximal end, and said socket having a proximal end having a face containing at least two openings with third and fourth diameters, said openings having seals associated therewith and said at least two openings capable of accepting the operating shafts of surgical instruments;

wherein said first diameter is greater than said second diameter.

2. The combination according to claim 1, characterized in that, said covering cap has elastic stop hooks extending essentially parallel to said socket, and ends on said hooks provided with projections for engagement with said cannula.

3. The combination according to claim 1, characterized in that said cap consists of elastic plastics material.

4. The combination according to claim 3, characterized in that the wall consists of silicone rubber.

5. The combination according to claim 1, characterized in that the wall is reinforced by a stabilization section between said openings.

6. The combination according to claim 1, characterized in that a closure is allocated to at least one of said openings.

7. The combination according to claim 6, characterized in that the closure is a stopper whose diameter is matched to at least one said opening.

8. The combination according to claim 7, characterized in that the stopper is secured to the covering cap by means of a flexible strip.

9. The combination according to claim 6, characterized in that the closure is designed as a sealing disk which elastically abuts against the edge of a said opening, which disk can be forced away in distal direction upon introduction of an operating instrument.

* * * * *